(12) United States Patent
Dalgleish et al.

(10) Patent No.: US 6,972,128 B1
(45) Date of Patent: Dec. 6, 2005

(54) USE OF HUMAN PROSTRATE CELL LINES IN PROSTATE CANCER TREATMENT

(75) Inventors: Angus George Dalgleish, London (GB); Peter Michael Smith, London (GB); Andrew Derek Sutton, London (GB); Anthony Ian Walker, London (GB)

(73) Assignee: Onyvax Limited, London (GB)

( * ) Notice: Subject to any disclaimer, the term of this patent is extended or adjusted under 35 U.S.C. 154(b) by 0 days.

(21) Appl. No.: 09/857,691

(22) PCT Filed: Dec. 9, 1999

(86) PCT No.: PCT/GB99/04129

§ 371 (c)(1),
(2), (4) Date: Sep. 5, 2001

(87) PCT Pub. No.: WO00/33869

PCT Pub. Date: Jun. 15, 2000

(30) Foreign Application Priority Data

Dec. 10, 1998 (GB) .................................... 9827104

(51) Int. Cl.$^7$ ............................................. A61K 35/12
(52) U.S. Cl. .................................. 424/277.1; 424/93.3
(58) Field of Search .............................. 424/93.1, 93.7, 424/573, 277.1

(56) References Cited

FOREIGN PATENT DOCUMENTS

WO       WO 93/06867    *  4/1993

OTHER PUBLICATIONS

Berthon, P et al, 1995, Intl J Oncology, 6(2): 333-343.*
Drexler et al (Leukemia and Lymphoma, 1993, 9:1-25).*
Embleton et al (Immunol Ser, 1984, 23:181-207).*
Hsu (in Tissue Culture Methods and Applications, Kruse and Patterson, Eds, 1973, Academic Press, NY, see abstract, p. 764).*
Freshney (Culture of Animal Cells, A Manual of Basic Technique, Alan R. Liss, Inc., 1983, New York, p4).*
Dermer (Bio/Technology, 1994, 12:320).*
Gura (Science, 1997, 278:1041-1042).*
Jain (Sci. Am., 1994, 271:58-65).*
Curti (Crit. Rev. in Oncology/Hematology, 1993, 14:29-39).*

(Continued)

Primary Examiner—Jeffrey Siew
Assistant Examiner—Misook Yu
(74) Attorney, Agent, or Firm—Heller Ehrman LLP (57) ABSTRACT

The invention here relates to a product comprised of a cell line or lines intended for use as an allogeneic immunotherapy agent for the treatment of cancer in mammals and humans. All of the studies of cell-based cancer vaccines to date have one feature in common, namely the intention to use cells that contain at least some TSAs and/or TAAs that are shared with the antigens present in patients' tumour. In each case, tumour cells are utilised as the starting point on the premise that only tumour cells will contain TSAs or TAAs of relevance, and the tissue origins of the cells are matched to the tumour site in patients. A primary aspect of the invention is the use of immortalised normal, non-malignant cells as the basis of an allogeneic cell cancer vaccine. Normal cells do not possess TSAs or relevant concentrations of TAAs and hence it is surprising that normal cells are effective as anti-cancer vaccines. For prostate cancer, for example, a vaccine may be based on one or a combination of different immortalised normal cell lines derived from the prostate. The cell lines are lethally irradiated utilising gamma irradiation at 50–300 Gy to ensure that they are replication incompetent prior to use in the mammal or human.

4 Claims, 10 Drawing Sheets

OTHER PUBLICATIONS

Hartwell et al (Science, 1997, 278:1064-1068).*
Wu TT et al, 1998, Intl J cancer, 77(6): 887-94.*
Triest JA et al, 1998, Clinical Cancer Res, 4(8): 2009-14.*
Boon (Adv Can Res, 1992, 58:177-210).*
The General Cell Collection on ECACC No. 95012613 downloaded on Apr. 5, 2005 from URL>http://www.ecacc.org.uk.*
ATCC accession number CRL-1740 downloaded on Apr. 5, 2005 from URL>http://www.atcc.org/catalog/numSearch/numResults.cfm?atccNum=CRL-1740.*
Ablin, J. Cancer Res. Clin. Oncol. 123: 583-594 (1997).
Tjoa et al., The Prostate 27: 63-69 (1995).
Vieweg et al., Cancer Research 54: 1760-1765 (1994).
Brenner et al., Journal of Urology, pp. 1575-1579 (1995) (abstract only).
Gorelik et al., Journal of Supramolecular Structure 12: 385-402 (1979) (abstract only).
Marble, Cancer Weekly Plus, p4(2) (1997).
Moran, American Medical News 42, 39, 23 (1999).

* cited by examiner

FIG. 1A
1T Cell proliferation Data for Patient 112

FIG. 1B
1T Cell proliferation Data for Patient 307

FIG. 2A
Western Blot Analysis of Serum From Patient 115
Patient 115 Pre Vaccination    Patient 115 Post Vaccination 1=Molecular weight markers, 2=PNT2 lysate,
3=1542 lysate, 4=DU145 lysate, 5=LnCap lysate

FIG. 2B
Western Blot Analysis of Serum From Patient 304
Patient 304 Pre Vaccination    Patient 304 Post Vaccination 1=Molecular weight markers, 2=PNT2 lysate, FIG. 3A Antibody Titres of Serum From Patient 112

FIG. 3B
Antibody Titres of Serum From Patient 305

FIG. 3C
Antibody Titres of Serum From Patient 402

FIG. 4A

Patient 110 — PSA Data for Patient 110

FIG. 4B

Patient 303 — PSA Data for Patient 303

FIG. 4C
PSA Data for Patient 404

FIG. 5
Survival Curves for C57 Mice Immunised With Normal Melanocytes

USE OF HUMAN PROSTRATE CELL LINES IN PROSTATE CANCER TREATMENT

This application is a 371 of PCT/GB99/04129 filed on Dec. 9, 1999, which is hereby incorporated by reference.

FIELD OF THE INVENTION

This invention is concerned with agents for the treatment of primary, metastatic and residual cancer in mammals (including humans) by inducing the immune system of the mammal or human afflicted with cancer to mount an attack against the tumour lesion. In particular, the invention pertains to the use of whole-cells, derivatives and portions thereof with or without vaccine adjuvants and/or other accessory factors. More particularly, this disclosure describes the use of particular combinations of whole-cells and derivatives and portions thereof that form the basis of treatment strategy.

BACKGROUND TO THE INVENTION

It is known in the field that cancerous cells contain numerous mutations, qualitative and quantitative, spatial and temporal, relative to their normal, non-cancerous counterparts and that at certain periods during tumour cells' growth and spread a proportion of these are capable of being recognised by the hosts' immune system as abnormal. This has led to numerous research efforts world-wide to develop immunotherapies that harness the power of the hosts' immune system and direct it to attack the cancerous cells, thereby eliminating such aberrant cells at least to a level that is not life-threatening (reviewed in Maraveyas, A. & Dalgleish, A. G. 1977 *Active immunotherapy for solid tumours in vaccine design* in The Role of Cytokine Networks, Ed. Gregoriadis et al., Plenum Press, New York, pages 129–145; Morton, D. L. and Ravindranath, M. H. 1996 *Current concepts concerning melanoma vaccines* in Tumor Immunology—Immunotherapy and Cancer Vaccines, ed. Dalgleish, A. G. and Browning, M., Cambridge University Press, pages 241–268. See also other papers in these publications for further detail).

Numerous approaches have been taken in the quest for cancer immunotherapies, and these can be classified under five categories:

Non-specific immunotherapy

Efforts to stimulate the immune system non-specifically date back over a century to the pioneering work of William Coley (Coley, W. B., 1894 Treatment of inoperable malignant tumours with toxins of erisipelas and the *Bacillus prodigosus*. Trans. Am. Surg. Assoc. 12: 183). Although successful in a limited number of cases (e.g. BCG for the treatment of urinary bladder cancer, IL-2 for the treatment of melanoma and renal cancer) it is widely acknowledged that non-specific immunomodulation is unlikely to prove sufficient to treat the majority of cancers. Whilst non-specific immune-stimulants may lead to a general enhanced state of immune responsiveness, they lack the targeting capability and also subtlety to deal with tumour lesions which have many mechanisms and plasticity to evade, resist and subvert immune-surveillance.

Antibodies and monoclonal antibodies

Passive immunotherapy in the form of antibodies, and particularly monoclonal antibodies, has been the subject of considerable research and development as anti-cancer agents. Originally hailed as the magic bullet because of their exquisite specificity, monoclonal antibodies have failed to live up to their expectation in the field of cancer immunotherapy for a number of reasons including immune responses to the antibodies themselves (thereby abrogating their activity) and inability of the antibody to access the lesion through the blood vessels. To date, three products have been registered as pharmaceuticals for human use, namely Panorex (Glaxo-Wellcome), Rituxan (IDEC/Genentech/Hoffman la Roche) and Herceptin (Genentech/Hoffman la Roche) with over 50 other projects in the research and development pipeline. Antibodies may also be employed in active immunotherapy utilising anti-idiotype antibodies which appear to mimic (in an immunological sense) cancer antigens. Although elegant in concept, the utility of antibody-based approaches may ultimately prove limited by the phenomenon of 'immunological escape' where a subset of cancer cells in a mammalian or human subject mutates and loses the antigen recognised by the particular antibody and thereby can lead to the outgrowth of a population of cancer cells that are no longer treatable with that antibody.

Subunit vaccines

Drawing on the experience in vaccines for infectious diseases and other fields, many researchers have sought to identify antigens that are exclusively or preferentially associated with cancer cells, namely tumour specific antigens (TSA) or tumour associated antigens (TAA), and to use such antigens or fractions thereof as the basis for specific active immunotherapy.

There are numerous ways to identify proteins or peptides derived therefrom which fall into the category of TAA or TSA. For example, it is possible to utilise differential display techniques whereby RNA expression is compared between tumour tissue and adjacent normal tissue to identify RNAs which are exclusively or preferentially expressed in the lesion. Sequencing of the RNA has identified several TAA and TSA which are expressed in that specific tissue at that specific time, but therein lies the potential deficiency of the approach in that identification of the TAA or TSA represents only a "snapshot" of the lesion at any given time which may not provide an adequate reflection of the antigenic profile in the lesion over time. Similarly a combination of cytotoxic T lymphocyte (CTL) cloning and expression-cloning of cDNA from tumour tissue has lead to identification of many TAA and TSA, particularly in melanoma. The approach suffers from the same inherent weakness as differential display techniques in that identification of only one TAA or TSA may not provide an appropriate representation of a clinically relevant antigenic profile.

Over fifty such subunit vaccine approaches are in development for the treatment of a wide range of cancers, although none has yet received marketing authorisation for use as a human pharmaceutical product. In a similar manner to that described for antibody-based approaches above, subunit vaccines may also be limited by the phenomenon of immunological escape.

Gene therapy

The majority of gene therapy trials in human subjects have been in the area of cancer treatment, and of these a substantial proportion have been designed to trigger and/or amplify patients' immune responses. Of particular note in commercial development are Allovectin-7 and Leuvectin, being developed by Vical Inc for a range of human tumours, CN706 being developed by Calydon Inc for the treatment of prostate cancer, and StressGen Inc.'s stress protein gene therapy for melanoma and lung cancer. At the present time, it is too early to judge whether these and the many other 'immuno-gene therapies' in development by commercial and academic bodies will ultimately prove successful, but it is widely accepted that commercial utility of these approaches are likely to be more than a decade away.

Cell-based vaccines

Tumours have the remarkable ability to counteract the immune system in a variety of ways including: downregulation of the expression of potential target proteins; mutation of potential target proteins; downregulation of surface expression of receptors and other proteins; downregulation of MHC class I and II expression thereby disallowing direct presentation of TAA or TSA peptides; downregulation of co-stimulatory molecules leading to incomplete stimulation of T-cells leading to anergy; shedding of selective, non representative membrane portions to act as decoy to the immune system; shedding of selective membrane portions to anergise the immune system; secretion of inhibitory molecules; induction of T-cell death; and many other ways. What is clear is that the immunological heterogeneity and plasticity of tumours in the body will have to be matched to a degree by immunotherapeutic strategies which similarly embody heterogeneity. The use of whole cancer cells, or crude derivatives thereof, as cancer immunotherapies can be viewed as analogous to the use of whole inactivated or attenuated viruses as vaccines against viral disease. The potential advantages are:

(a) whole cells contain a broad range of antigens, providing an antigenic profile of sufficient heterogeneity to match that of the lesions as described above;

(b) being multivalent (i.e. containing multiple antigens), the risk of immunological escape is reduced (the probability of cancer cells 'losing' all of these antigens is remote); and (c) cell-based vaccines include TSAs and TAAs that have yet to be identified as such; it is possible if not likely that currently unidentified antigens may be clinically more relevant than the relatively small number of TSAs/TAAs that are known.

Cell-based vaccines fall into two categories. The first, based on autologous cells, involves the removal of a biopsy from a patient, cultivating tumour cells in vitro, modifying the cells through transfection and/or other means, irradiating the cells to render them replication-incompetent and then injecting the cells back into the same patient as a vaccine. Although this approach enjoyed considerable attention over the past decade, it has been increasingly apparent that this individually-tailored therapy is inherently impractical for several reasons. The approach is time consuming (often the lead time for producing clinical doses of vaccine exceeds the patients' life expectancy), expensive and, as a 'bespoke' product, it is not possible to specify a standardised product (only the procedure, not the product, can be standardised and hence optimised and quality controlled). Furthermore, the tumour biopsy used to prepare the autologous vaccine will have certain growth characteristics, interactions and communication with surrounding tissue that makes it somewhat unique. This alludes to a potentially significant disadvantage to the use of autologous cells for immunotherapy: a biopsy which provides the initial cells represents an immunological snapshot of the tumour, in that environment, at that point in time, and this may be inadequate as an immunological representation over time for the purpose of a vaccine with sustained activity that can be given over the entire course of the disease.

The second type of cell-based vaccine and the subject of the current invention describes the use of allogeneic cells which are be genetically (and hence immunologically) mismatched to the patients. Allogeneic cells benefit from the same advantages of multivalency as autologous cells. In addition, as allogeneic cell vaccines can be based on immortalised cell lines which can be cultivated indefinitely in vitro, thus this approach does not suffer the lead-time and cost disadvantages of autologous approaches. Similarly the allogeneic approach offers the opportunity to use combinations of cells types which may match the disease profile of an individual in terms of stage of the disease, the location of the lesion and potential resistance to other therapies.

There are numerous published reports of the utility of cell-based cancer vaccines (see, for example, Dranoff, G. et al. WO 93/06867; Gansbacher, P. WO 94/18995; Jaffee, E. M. et. al. WO 97/24132; Mitchell, M. S. WO 90/03183; Morton, D. M. et. al WO 91/06866). These studies encompass a range of variations from the base procedure of using cancer cells as an immunotherapy antigen, to transfecting the cells to produce GM-CSF, IL-2, interferons or other immunologically-active molecules and the use of 'suicide' genes. Groups have used allogeneic cell lines that are HLA-matched or partially-matched to the patients' haplotype and also allogeneic cell lines that are mismatched to the patients' haplotype in the field of melanoma and also mismatched alogeneic prostate cell lines transfected with GM-CSF.

DESCRIPTION OF THE INVENTION

The invention disclosed here relates to a product comprised of a cell line or lines intended for use as an allogeneic immunotherapy agent for the treatment of cancer in mammals and humans.

All of the studies of cell-based cancer vaccines to date have one feature in common, namely the intention to use cells that contain at least some TSAs and/or TAAs that are shared with the antigens present in patients' tumour. In each case, tumour cells are utilised as the starting point on the premise that only tumour cells will contain TSAs or TAAs of relevance, and the tissue origins of the cells are matched to the tumour site in patients.

A primary aspect of the invention is the use of immortalised normal, non-malignant cells as the basis of an allogeneic cell cancer vaccine. Normal cells do not posses TSAs or relevant concentrations of TAAs and hence it is surprising that normal cells as described herein are effective as anticancer vaccines. The approach is general and can be adapted to any mammalian tumour by the use of immortalised normal cells derived from the same particular tissue as the tumour intended to be treated. Immortalised normal cells can be prepared by those skilled in the art using published methodologies, or they can be sourced from cell banks such as ATCC or ECACC, or they are available from several research groups in the field.

For prostate cancer, for example, a vaccine may be based on one or a combination of different immortalised normal cell lines derived from the prostate which can be prepared using methods reviewed and cited in Rhim, J. S. and Kung, H-F., 1997 Critical Reviews in Oncogenesis 8(4):305–328 or selected from PNT1A (ECACC Ref No: 95012614), PNT2 (ECACC Ref No: 95012613) or PZ-HPV-7 (ATCC Number: CRL-2221).

A further aspect of the invention is the addition of TSAs and/or TAAs by combining one or more immortalised normal cell line(s) with one, two or three different cell lines derived from primary or metastatic cancer biopsies.

All the appropriate cell lines will show good growth in large scale cell culture and sufficient characterisation to allow for quality control and reproducible production.

The cell lines are lethally irradiated utilising gamma irradiation at 50–300 Gy to ensure that they are replication incompetent prior to use in the mammal or human.

The cell lines and combinations referenced above, to be useful as immunotherapy agents must be frozen to allow transportation and storage, therefore a further aspect of the invention is any combination of cells referenced above formulated with a cryoprotectant solution. Suitable cryoprotectant solutions may include but are not limited to, 10–30% v/v aqueous glycerol solution, 5–20% v/v dimethyl sulphoxide or 5–20% w/v human serum albumin may be used either as single cryoprotectants or in combination.

A further embodiment of the invention is the use of the cell line combinations with non-specific immune stimulants such as BCG or M. Vaccae, Tetanus toxoid, Diphtheria toxoid, *Bordetella Pertussis*, interleukin 2, interleukin 12, interleukin 4, interleukin 7, Complete Freund's Adjuvant, Incomplete Freund's Adjuvant or other non-specific agents known in the art. The advantage is that the general immune stimulants create a generally enhanced immune status whilst the combinations of cell lines, both add to the immune enhancement through their haplotype mismatch and target the immune response to a plethora of TAA and TSA as a result of the heterogeneity of their specific origins.

The invention will now be described with reference to the following examples, and the Figures in which.

EXAMPLE 1

Growth, irradiation, formulation and storage of cells

An immortalised cell line derived from normal prostate tissue namely PNT2 was grown in roller bottle culture in RPMI 1640 medium supplemented with 2 mM L-glutamine and 5% foetal calf serum (FCS) following recovery from liquid nitrogen stocks. Following expansion in T175 static flasks the cells were seeded into roller bottles with a growth surface area of 850 cm$^2$ at 1–20×10$^7$ cells per roller bottle.

An immortalised cell line derived from primary prostate tissue namely NIH1542-CP3TX was grown in roller bottle culture in KSFM media supplemented with 25 µg/ml bovine pituitary extract, 5 ng/ml of epidermal growth factor, 2 mM L-glutamine, 10 mM HEPES buffer and 5% foetal calf serum (FCS) (hereinafter called "modified KSFM") following recovery from liquid nitrogen stocks. Following expansion in T175 static flasks the cells were seeded into roller bottles with a growth surface area of 1,700 cm$^2$ at 2–5×10$^7$ cells per roller bottle.

Two secondary derived cell lines were also used, namely LnCap and Du145 both of which were sourced from ATCC. LnCap was grown in large surface area static flasks in RPMI media supplemented with 10% FCS and 2 mM L-glutamine following seeding at 1–10×10$^6$ cells per vessel and then grown to near confluence. Du-145 was expanded from frozen stocks in static flasks and then seeded into 850 cm$^2$ roller bottles at 1–20×10$^7$ cells per bottle and grown to confluence in DMEM medium containing 10% FCS and 2 mM L-glutamine. All cell lines were harvested utilising trypsin at 1× normal concentration. Following extensive washing in DMEM the cells were re-suspended at a concentration of 5–40×10$^6$ cells/ml and irradiated at 50–300 Gy using a Co$^{60}$ source. Following irradiation the cells were formulated in cryopreservation solution composing of 10% DMSO, 8% human serum albumin in phosphate buffered saline, and frozen at a cell concentration of 5–150×10$^6$ cells/ml, in liquid nitrogen until required for use.

Vaccination

Prostate cancer patients were selected on the basis of being refractory to hormone therapy with a serum PSA level of at least 30 ng/ml. Ethical permission and MCA (UK Medicines Control Agency) authorization were sought and obtained to conduct this trial.

One of three vaccination schedules was followed for each arm of the trial:

| | Cell Lines Administered | | |
|---|---|---|---|
| Dose | Trial Arm A | Trial Arm B | Trial Arm C |
| 1,2 and 3 | PNT2 | Du145 | LnCap |
| 4 and subsequent | PNT2/Du145/NIH1542 | PNT2/Du145/LnCap | PNT2/NIH1542/LnCap |

The cells were warmed gently in a water bath at 37° C. and admixed with mycobacterial adjuvant prior to injection into patients. Injections were made intra-dermally at four injection sites into draining lymph node basins. The minimum interval between doses was two weeks, and most of the doses were given at intervals of four weeks. Prior to the first dose, and prior to some subsequent doses, the patients were tested for delayed-type hypersensitivity (DTH) against the four cell lines listed in the vaccination schedule above (all tests involved 0.8×10$^6$ cells with no adjuvant).

Analysis of Immunological Response (a) T-Cell Proliferation Responses

To determine if vaccination resulted in a specific expansion of T-cell populations that recognised antigens derived from the vaccinating cell lines we performed a proliferation assay on T-cells following stimulation with lysates of the prostate cell lines. Whole blood was extracted at each visit to the clinic and used in a BrdU (bromodeoxyuridine) based proliferation assay as described below:

| Patient BrdU proliferation method Reagents | | |
|---|---|---|
| RPMI | | Life Technologies, Paisley Scotland. |
| BrdU | | Sigma Chemical Co, Poole, Dorset. |
| PharMlyse | 35221E | Pharmingen, Oxford UK |
| Cytofix/Cytoperm | 2090KZ | " |
| Perm/Wash buffer (×10) | 2091KZ | " |
| FITC Anti-BrdU/Dnase | 340649 | Becton Dickinson |
| PerCP Anti-CD3 | 347344 | " |
| Pe Anti-CD4 | 30155X | Pharmingen |
| Pe Anti-CD8 | 30325X | " |
| FITC mu-IgG1 | 349041 | Becton Dickinson |
| PerCP IgG1 | 349044 | " |
| PE IgG1 | 340013 | " |

Method
1) Dilute 1 ml blood with 9 ml RPMI+2 mM L-gin+PS+50 µM 2-Me. Do not add serum. Leave overnight at 37° C.
2) On following morning, aliquot 450 µl of diluted blood into wells of a 48-well plate and add 50 µl of stimulator lysate. The lysate is made by freeze-thawing tumour cells (2×10$^6$ cell equivalents/ml) ×3 in liquid nitrogen and then storing aliquots frozen until required.
3) Culture cells at 37° C. for 5 days
4) On the evening of day 5 add 50 µl BrdU @ 30 µg/ml 5) Aliquot 100 µl of each sample into a 96-well round-bottomed plate.
6) Spin plate and discard supernatant
7) Lyse red cells using 100 µl Pharmlyse for 5 minutes at room temperature
8) Wash ×2 with 50 µl of Cytofix
9) Spin and remove supernatant by flicking
10) Permeabilise with 100 µl Perm wash for 10 mins at RT
11) Add 30 µl of antibody mix comprising antibodies at correct dilution made up to volume with Perm-wash
12) Incubate for 30 mins in the dark at room temperature.
13) Wash ×1 and resuspend in 100 µl 2% paraformaldehyde
14) Add this to 400 µl FACSFlow in cluster tubes ready for analysis
15) Analyse on FACScan, storing 3000 gated CD3 events.

| 6-well plate for stimulation | | | | | | |
|---|---|---|---|---|---|---|
| | Nil | ConA | 1542 | LnCap | Du145 | Pnt2 |
| PBL 1 | | | | | | |
| PBL 2 | | | | | | |
| PBL 3 | | | | | | |
| PBL 4 | | | | | | |
| PBL 5 | | | | | | |
| PBL 6 | | | | | | |

| 96-well plate for antibody staining | | | | | | | | | | | |
|---|---|---|---|---|---|---|---|---|---|---|---|
| PBL 1 | | PBL 2 | | PBL 3 | | PBL 4 | | PBL 5 | | PBL 6 | |
| Nil A | 15 D | Nil A | 15 D | Nil A | 15 D | Nil A | 15 D | Nil A | 15 D | Nil A | 15 D |
| Nil D | 15 E | Nil D | 15 E | Nil D | 15 E | Nil D | 15 E | Nil D | 15 E | Nil D | 15 E |
| Nil E | Ln D | Nil E | Ln D | Nil E | Ln D | Nil E | Ln D | Nil E | Ln D | Nil E | Ln D |
| Con D | Ln E | Con D | Ln E | Con D | Ln E | Con D | Ln E | Con D | Ln E | Con D | Ln E |
| Con E | Du D | Con E | Du D | Con E | Du D | Con E | Du D | Con E | Du D | Con E | Du D |
| | Du E | | Du E | | Du E | | Du E | | Du E | | Du E |
| | Pn D | | Pn D | | Pn D | | Pn D | | Pn D | | Pn D |
| | Pn E | | Pn E | | Pn E | | Pn E | | Pn E | | Pn E |

Figure 1A:
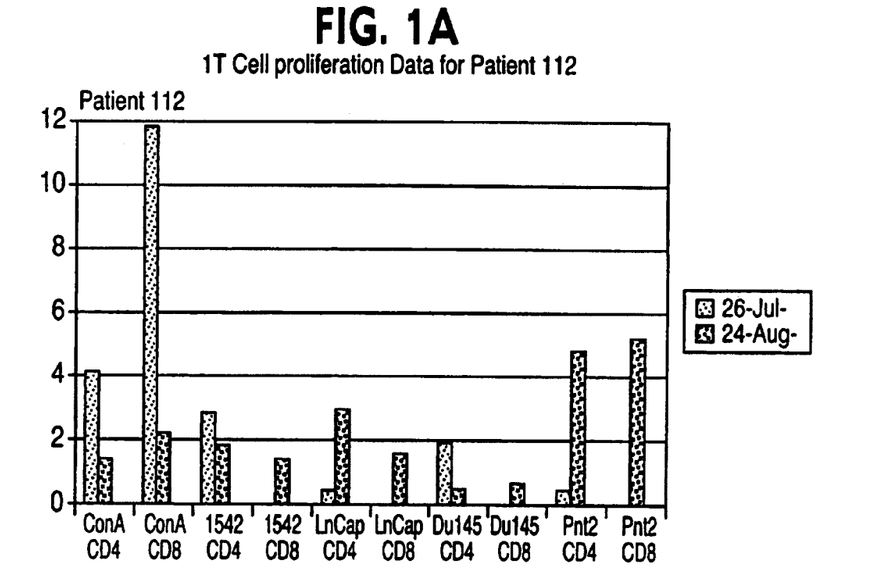
FIG. 1 shows T-cell proliferation data for patients 112, 307, and 406.
Figure 1B:
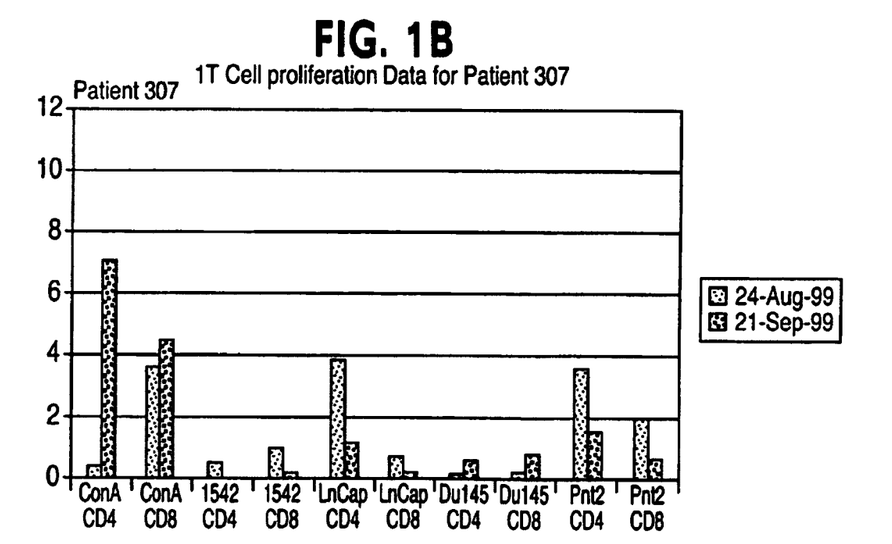
Figure 1C:
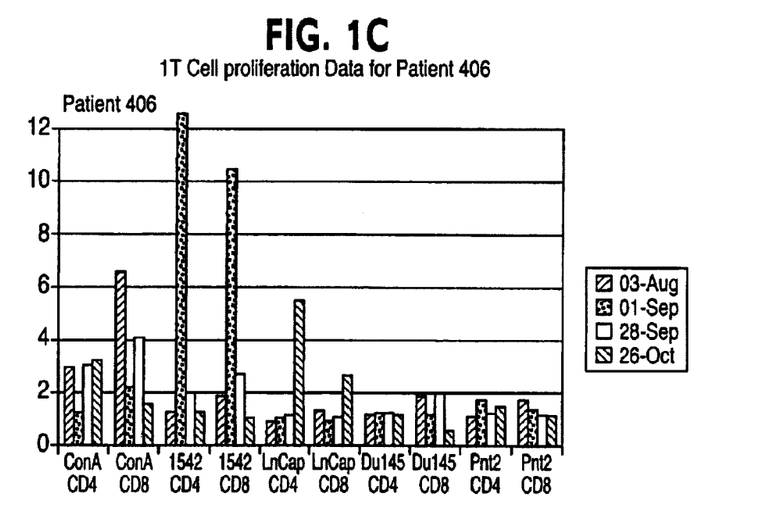
Figure 2A:
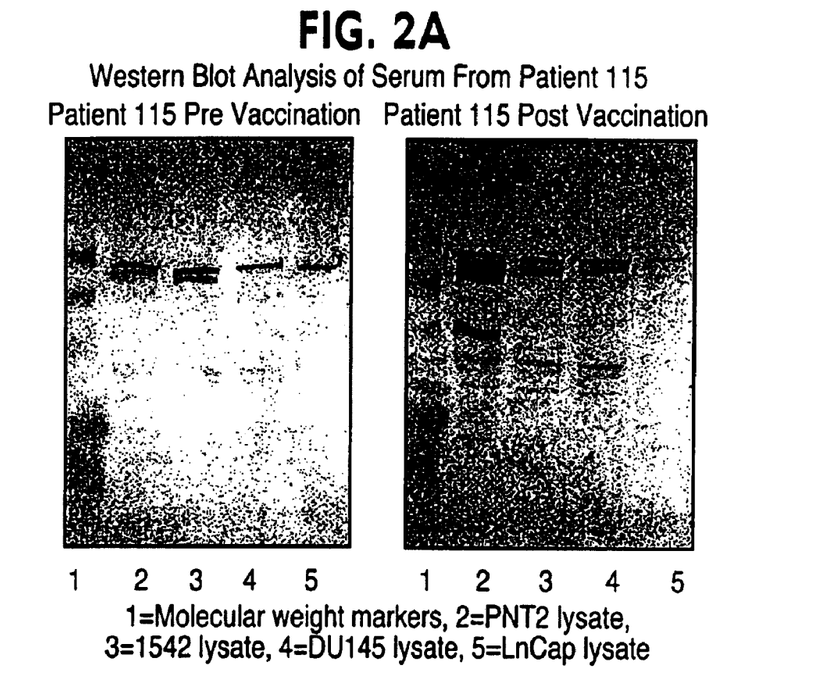
FIG. 2 shows Western Blot analysis of serum from patients 115, 304 and 402.
Figure 2B:
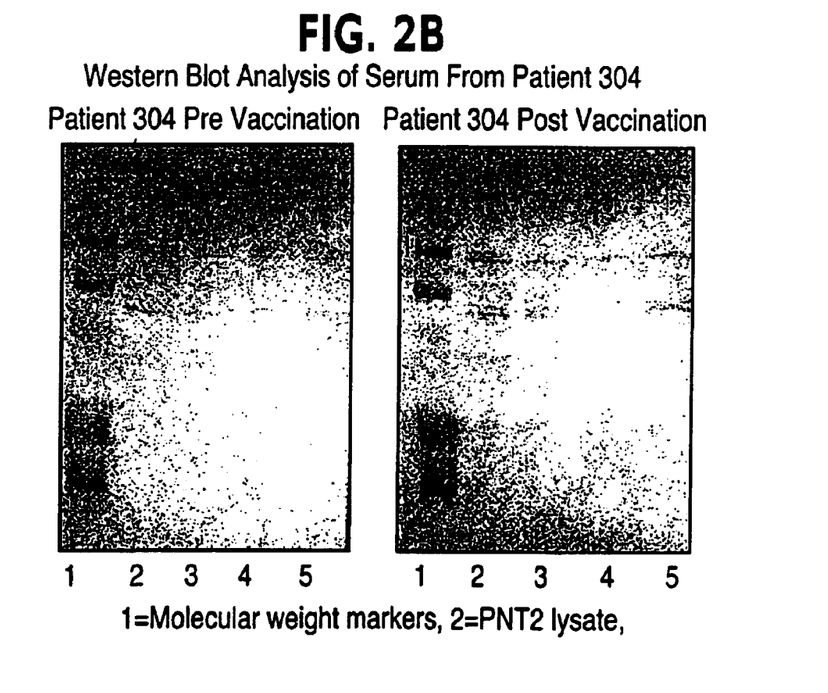
Figure 2C:
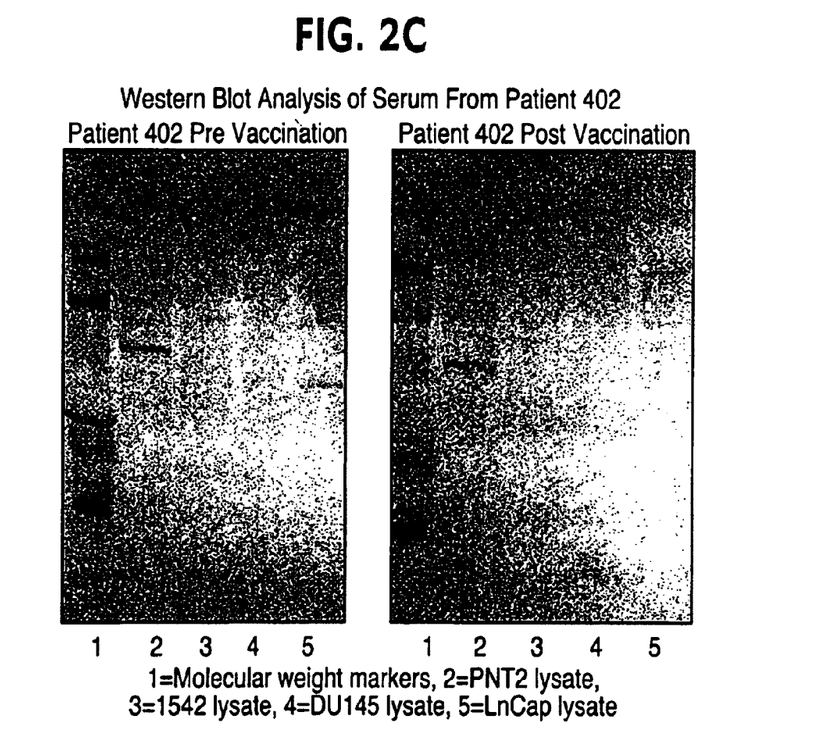

Legend:
A: IgG1-FITC (5 µl)
15 µl MoAb + 15 µl
IgG1-PE (5 µl)
IgG1-PerCP (5 µl)
D: BrdU-FITC (5 µl)
15 µl MoAb + 15 µl
CD4-PE (5 µl)
CD3-PerCP (5 µl)
E: BrdU-FITC (5 µl)
15 µl MoAb + 15 µl
CD8-PE (5 µl)
CD3-PerCP (5 µl)
15: NIH1542-CP3TX
Ln: LnCap
D: Du145
Pn: PNT2
Con: ConA lectin (positive control)
Nil: No stimulation The results for the proliferation assays are shown in FIG. 1 where a proliferation index for either CD4 or CD8 positive T-cells are plotted against the various cell lysates. The proliferation index being derived by dividing through the percentage of T-cells proliferating by the no-lysate control.

Results are shown for patient numbers 112, 307 and 406. Results are given for four cell lysates namely, NIH1542, LnCap, DU-145 and PNT-2. Overall, 50% of patients treated mount a specific proliferative response to at least one of the cell lines.

(b) Western Blots Utilising Patients' Serum

Standardised cell lysates were prepared for a number of prostate cell lines to enable similar quantities of protein to be loaded on a denaturing SDS PAGE gel for Western blot analysis. Each blot was loaded with molecular weight markers, and equal amounts of protein derived from cell lysates of NIH1542, LnCap, DU-145 and PNT-2. The blot was then probed with serum from patients derived from pre-vaccination and following 16 weeks vaccination (four to six doses).

Method a) Sample Preparation (Prostate Tumor Lines)
 Wash cell pellets 3 times in PBS
 Re-suspend at $1 \times 10^7$ cells/ml of lysis buffer
 Pass through 5 cycles of rapid freeze thaw lysis in liquid nitrogen/water bath
 Centrifuge at 1500 rpm for 5 min to remove cell debris
 Ultracentrifuge at 20,000 rpm for 30 min to remove membrane contaminants
 Aliquot at 200 µl and stored at −80° C.

b) Gel Electrophoresis
 Lysates mixed 1:1 with Laemelli sample buffer and boiled for 5 min
 20 µg samples loaded into 4–20% gradient gel wells
 Gels run in Bjerrum and Schafer-Nielson transfer buffer (with SDS) at 200 V for 35 min.

c) Western Transfer
 Gels, nitrocellulose membranes and blotting paper equilibrated in transfer buffer for 15 min
 Arrange gel-nitrocellulose sandwich on anode of semi-dry electrophoretic transfer cell: 2 sheets of blotting-paper, nitrocellulose membrane, gel, 2 sheets of blotting paper Apply cathode and run at 25 V for 90 min.

d) Immunological Detection of Proteins

Block nitrocellulose membranes overnight at 4° C. with 5% Marvel in PBS/0/05% Tween 20

Figure 3A:
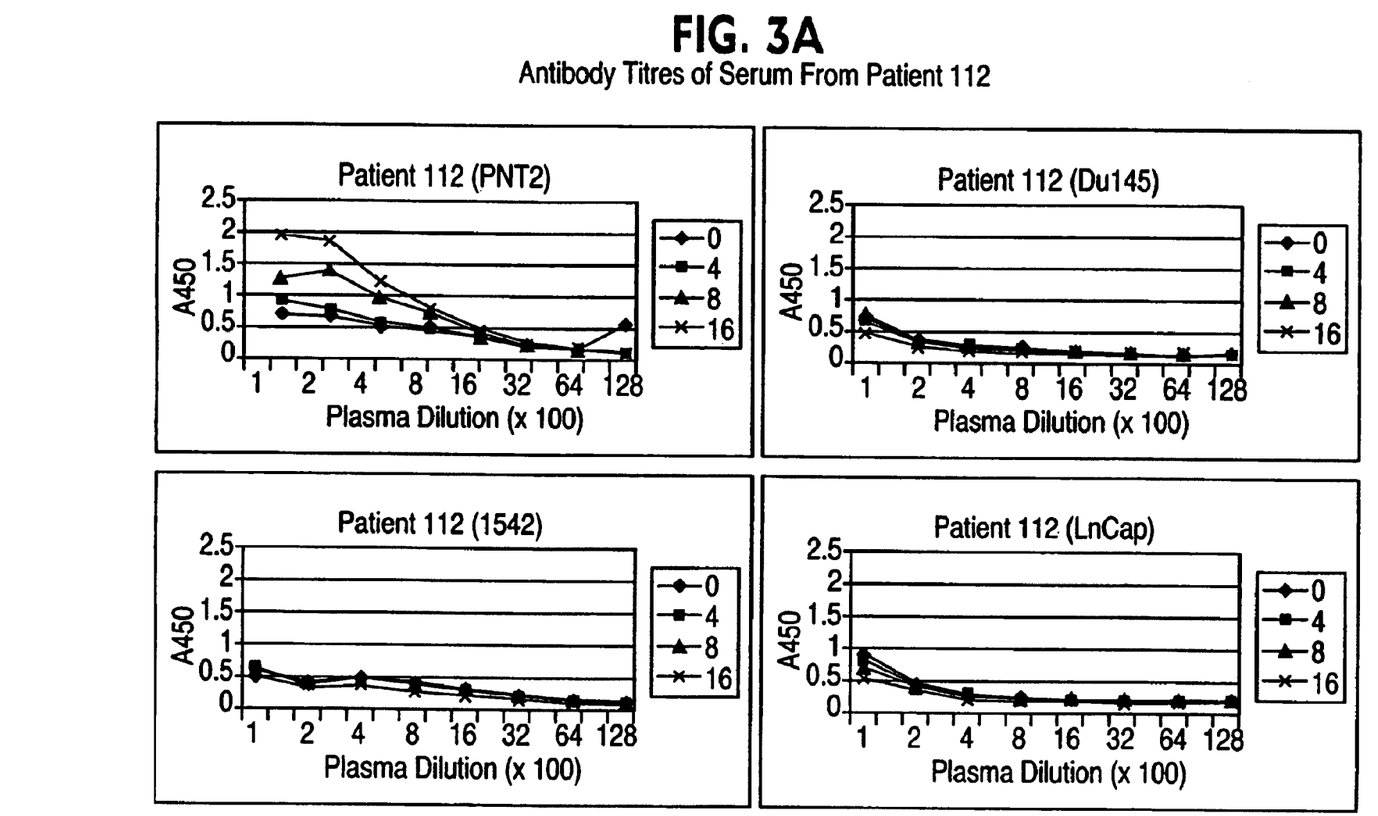
FIG. 3 shows antibody titres of serum from patients 112, 305 and 402.
Figure 3B:
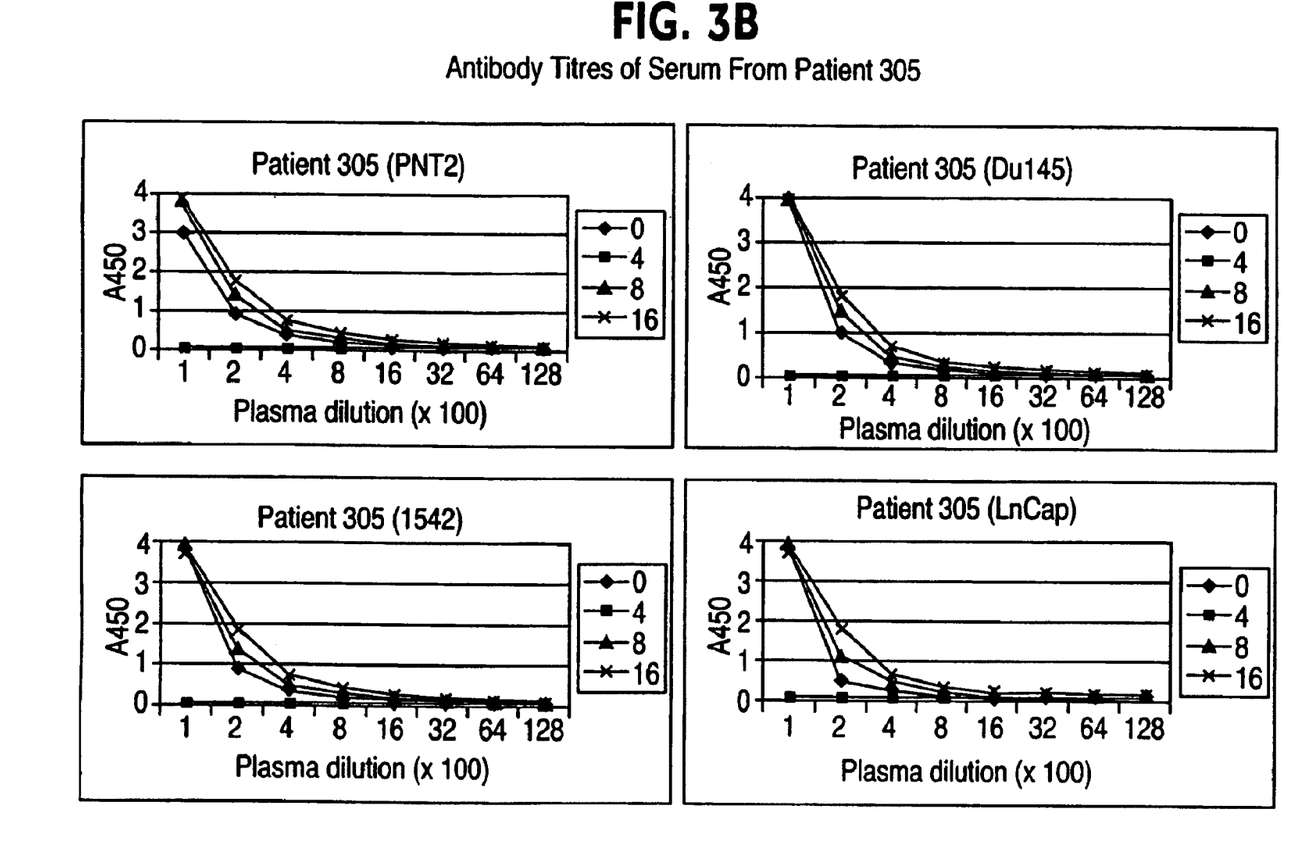
Figure 3C:
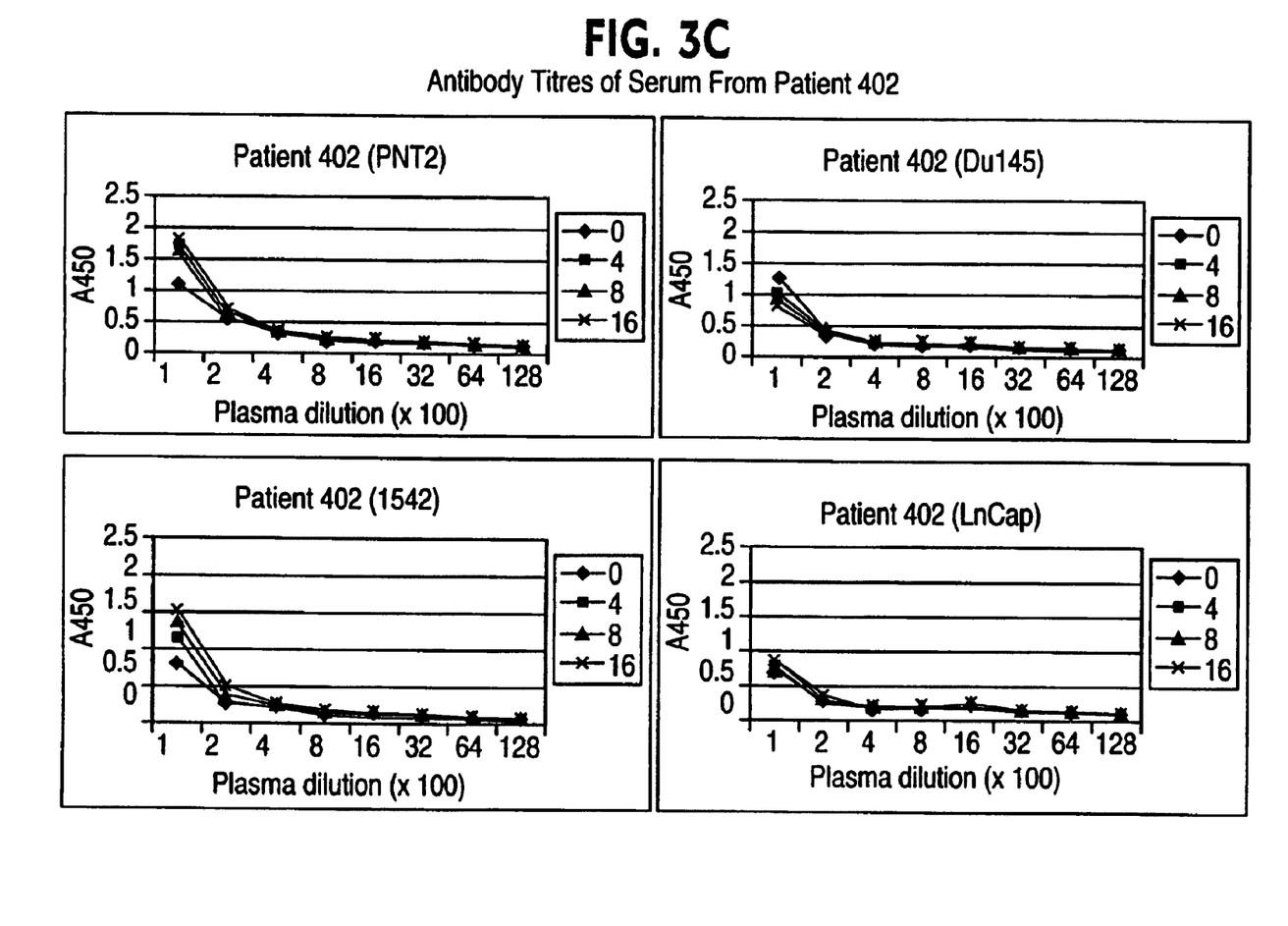

Rinse membranes twice in PBS/0.05% Tween 20, then wash for 20 min and 2×5 min at RT on a shaking platform Incubate membranes in 1:20 dilution of clarified patient plasma for 120 min at RT on a shaking platform Wash as above with an additional 5 min final wash Incubate membranes in 1:250 dilution of biotin anti-human IgG or IgM for 90 min at RT on a shaking platform Wash as above with an additional 5 min final wash Incubate membranes in 1:1000 dilution of streptavidin-horseradish peroxidase conjugate for 60 min at RT on a shaking platform Wash as above Incubate membranes in Diaminobenzidine peroxidase substrate for 5 min to allow colour development, stop reaction by rinsing membrane with water The results in FIG. 3 for patients 112, 305 and 402 clearly show that vaccination over the period of 16 weeks (four to six doses) can result in an increase in antibody titre against cell line lysates and also cross reactivity against lysates not received in this vaccination regime (other than DTH testing).

(c) Antibody Titre Determination

Antibody titres were determined by coating ELISA plates with standardised cell line lysates and performing dilution studies on serum from vaccinated patients.

Method for ELISA with anti-lysate IgG.

1. Coat plates with 50 µl/well lysates (@10 µg/ml) using the following dilutions:—

| Lysate | Protein conc | Coating conc | amount/ml | amount in 5 mls µl |
|---|---|---|---|---|
| PNT2 | 2.5 mg/ml | 10 µg/ml | 3.89 µl | 19.4 µl |
| 1542 | 4.8 mg/ml | 10 µg/ml | 2.07 µl | 10.3 µl |
| Du145 | 2.4 mg/ml | 10 µg/ml | 4.17 µl | 20.8 µl |
| LnCap | 2.4 mg/ml | 10 µg/ml | 4.12 µl | 20.6 µl |

2. Cover and incubate overnight @ 40° C.
3. Wash ×2 PBS-Tween. Pound plate on paper towels to dry.
4. Block with PBS/10% FCS (100 µl/well)
5. Cover and incubate @ room temperature (RT) for 1 hour (minimum).
6. Wash ×2 PBS-Tween
7. Add 100 µl PBS-10% FCS to rows 2–8
8. Add 200 µl plasma sample (diluted 1 in 100 in PBS-10% FCS ie. 10 µl plasma added to 990 µls PBS-10% FCS) to row 1 and do serial 100 µl dilutions down the plate as below. Discard extra 100 µl from bottom well. Cover and incubate in fridge overnight.
9. Dilute biotinylated antibody (Pharmingen; IgG 34162D) ie. final conc 1 mg/ml (ie 20 ml in 10 mls).
10. Cover and incubate @RT for 45 min.
11. Wash×6 as above.
12. Dilute streptavidin-HRP (Pharmingen, 13047E 0; dilute 1:1000 (ie 10 mL −>10 mls).
13. Add 100 ml/well.
14. Incubate 30 min @RT.
15. Wash×8.
16. Add 100 ml substrate/well. Allow to develop 10–80 min at RT.
17. Colour reaction stopped by adding 100 ml 1M $H_2SO_4$.
18. Read OD @ A405 nm.

The results in FIG. 3 for patients 112, 305 and 402 show antibody titres at baseline (O), 4 weeks, 8 weeks and 16 weeks. The data show that after vaccination with at least four doses, patients can show an increase in antibody titre against cell line lysates and also cross-reactivity against cell lines not received in this vaccination regime (except as DTH doses).

(d) Evaluation of PSA Levels

Figure 4A:
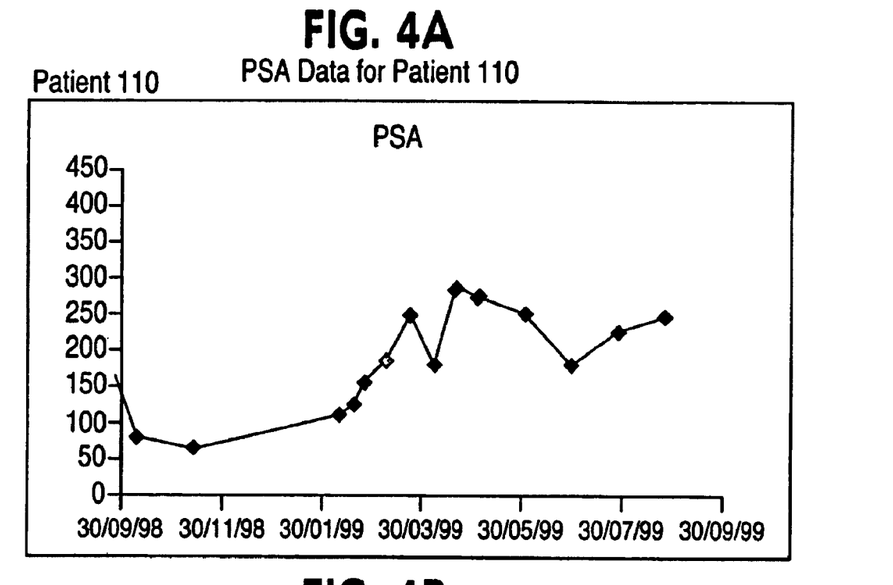
FIG. 4 shows PSA data for patients 110, 303 and 404.
Figure 4B:
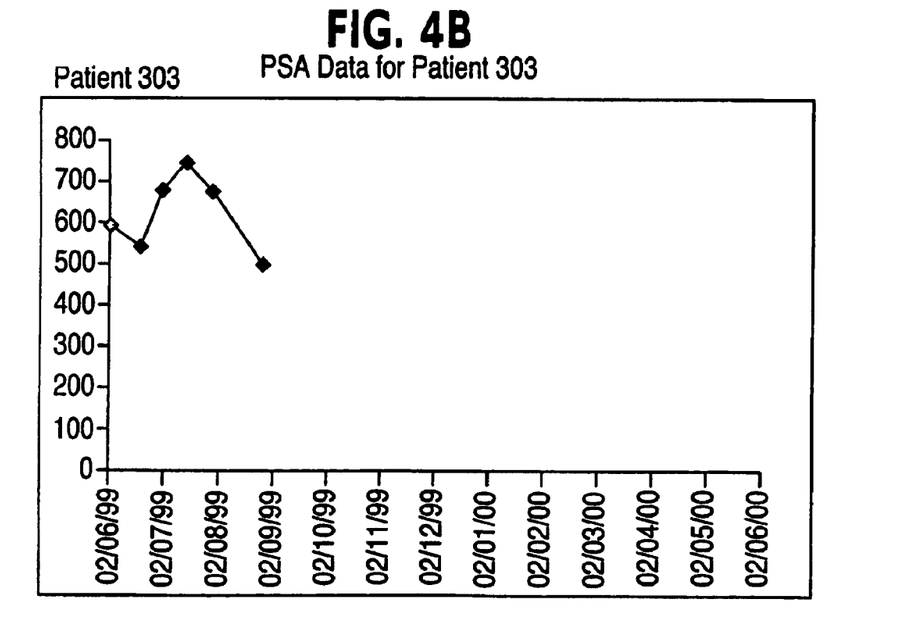
Figure 4C:
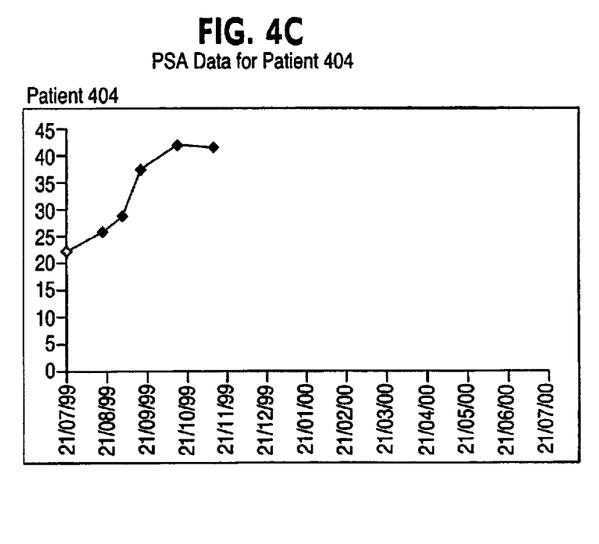

PSA levels for patients receiving the vaccine were recorded at entry into the trial and throughout the course of vaccination, using routinely used clinical kits. The PSA values for patients 110, 303 and 404 are shown in FIG. 4 (vertical axis is serum PSA in ng/ml; horizontal axis is time, with the first time point representing the initiation of the vaccination programme) and portray a drop or partial stabilisation of the PSA values, which in this group of patients normally continues to rise, often exponentially. The result for patient 110 is somewhat confound by the radiotherapy treatment to alleviate bone pain, although the PSA level had dropped prior to radiotherapy.

EXAMPLE 2

Use of a Norm Melanocyte in a Murine Melanoma Protection Model Model

Figure 5:
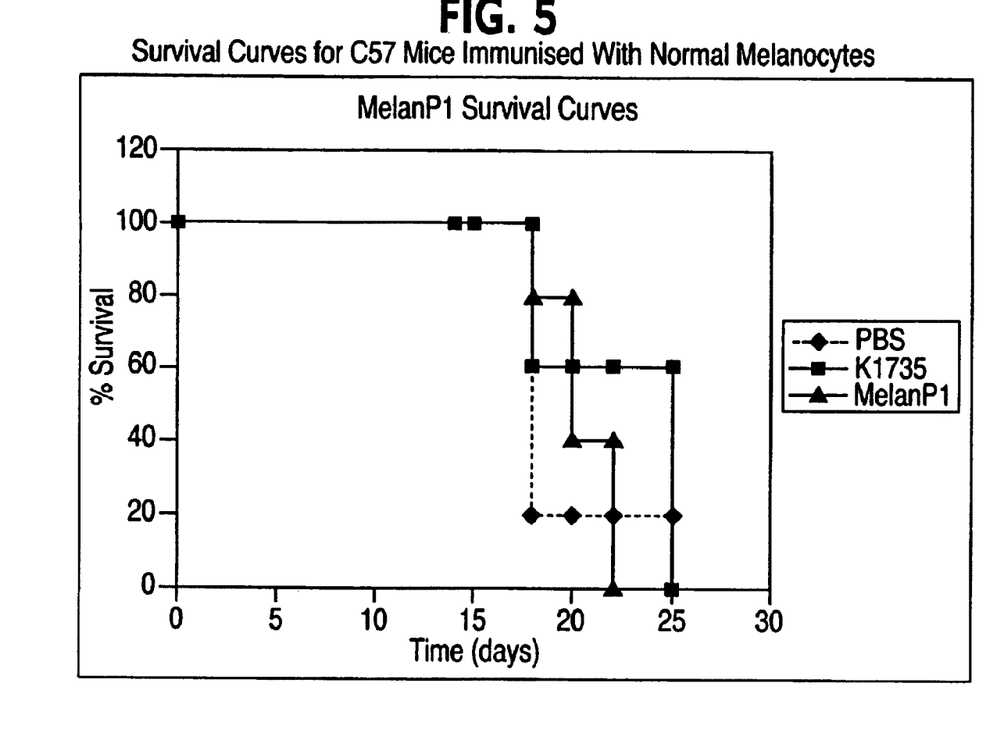
FIG. 5 shows survival curves for C57 mice immunised with normal melanocytes.

A normal melanocyte cell line was used in a vaccination protection model of murine melanoma utilising the B16.F10 as the challenge dose. The C57 mice received two vaccinations of either PBS, 5×10⁶ irradiated K1735 allogeneic melanoma cells or 5×10⁶ irradiated Melan P1 autologous normal melanocyte cells on days −14 and −7. Challenge on day 0 was with 1×10⁴ B16.F10 cells and tumour volume measured every three days from day 10 onwards. Animals were sacrificed when the tumour had grown to 1.5×1.5 cm measured across the maximum dimensions of the tumour. FIG. 5 shows that vaccination with Melan 1P cells offer some level of protection against this particularly aggressive murine tumour.

What is claimed is:

1. An allogeneic immunogenic agent comprising
   (a) normal prostate human PNT2 (ECACC 95012613),
   (b) primary prostate human NIH-1542 (ATCC CRL-12037), and
   (c) cancerous prostate human LNCap (ATCC CRL-1740).

2. An allogeneic immunogenic composition comprising (1) an allogeneic immunogenic agent comprising
   (a) normal prostate human PNT2 (ECACC 95012613),
   (b) primary prostate human NIH-1542 (ATCC CRL-12037), and
   (c) cancerous prostate human LNCap (ATCC CRL-1740) and (2) a vaccine adjuvant selected from the group consisting of BCG, M. Vaccae, Tetanus toxoid, Diphtheria toxoid, *Bordetella Pertussis*, interleukin 2, interleukin 12, interleukin 4, interleukin 7, Complete Freund's Adjuvant, Incomplete Freund's Adjuvant, and non-specific adjuvants.

3. An immunogenic composition comprising (1) an allogeneic immunogenic agent comprising
   (a) normal prostate human PNT2 (ECACC 95012613), (b) primary prostate human NIH-1542 (ATCC CRL-12037), and
(c) cancerous Prostate human LNCap (ATCC CRL-1740) and (2) a vaccine adjuvant, wherein the adjuvant is a mycobacterial preparation.

4. The allogeneic immunogenic agent of claim 1, wherein the cell lines are rendered replication-incompetent by irradiation.

* * * * *